(12) United States Patent
Granger et al.

(10) Patent No.: US 12,133,861 B2
(45) Date of Patent: Nov. 5, 2024

(54) NAIL COMPOSITIONS HAVING ANTIFUNGAL PROPERTIES

(71) Applicant: ISDIN, S.A., Barcelona (ES)

(72) Inventors: Corinne Jeanne Rose Granger, Barcelona (ES); Carlos Ramon Trullas Cabanas, Barcelona (ES)

(73) Assignee: ISDIN, S.A., Barcelona (ES)

( * ) Notice: Subject to any disclaimer, the term of this patent is extended or adjusted under 35 U.S.C. 154(b) by 715 days.

(21) Appl. No.: 17/420,332

(22) PCT Filed: Jan. 7, 2020

(86) PCT No.: PCT/EP2020/050215
§ 371 (c)(1),
(2) Date: Jul. 1, 2021

(87) PCT Pub. No.: WO2020/144185
PCT Pub. Date: Jul. 16, 2020

(65) Prior Publication Data
US 2022/0088060 A1 Mar. 24, 2022

(30) Foreign Application Priority Data
Jan. 8, 2019 (EP) .................................... 19382010

(51) Int. Cl.
*A61K 31/728* (2006.01)
*A61K 9/00* (2006.01)
*A61K 47/32* (2006.01)
*A61P 31/00* (2006.01)

(52) U.S. Cl.
CPC .......... *A61K 31/728* (2013.01); *A61K 9/0014* (2013.01); *A61K 47/32* (2013.01); *A61P 31/00* (2018.01)

(58) Field of Classification Search
CPC ...... A61K 31/715; A61K 8/585; A61K 36/22; A61K 8/735; A61K 31/728; A61K 9/0014; A61K 9/7015
See application file for complete search history.

(56) References Cited

U.S. PATENT DOCUMENTS

| | | | |
|---|---|---|---|
| 6,264,926 B1 | 7/2001 | Farooqi et al. | |
| 10,881,127 B1 * | 1/2021 | Mun | A23L 2/68 |
| 2015/0250698 A1 | 9/2015 | Dalko et al. | |
| 2016/0220728 A1 | 8/2016 | Adams et al. | |
| 2018/0256603 A1 * | 9/2018 | Hazan | A61K 31/569 |

FOREIGN PATENT DOCUMENTS

| | | |
|---|---|---|
| DE | 102006049585 A1 | 4/2008 |
| FR | 2989274 | 10/2013 |
| FR | 3060005 A1 | 6/2018 |
| KR | 2010-026835 A | 3/2010 |
| KR | 2010-0060599 A | 6/2010 |

OTHER PUBLICATIONS

EPO Communication pursuant to Article 94(3) EPC dated Nov. 16, 2021 for European Patent Application No. 20700649.5; 4 pages.
Database GNPD [online] Minte; Nov. 23, 2013; Anonymous: "Supreme Reviving Cream", XP055859612; Database accession No. 2245093; 5 pages.
Database GNPD [online] Minte; Mar. 12, 2018; Anonymous: "Cicabio Cream", XP055859617; Database accession No. 5510123; 4 pages.
Database European Commission/Cosmetics—CosIng Internal Market, Industry, Entrepreneurship and SMEs; Ingredient Pistacia Lentiscus Gum; one page. (No date available. Cited to Applicant on Feb. 21, 2023) https://ec.europa.eu/growth/tools-databases/cosing/index.cfm?fuseaction=search.details_v2&id=59569.
"EGF Active: Recovery Milk™ Toleriane Soothing Repairing Cream," Chinese National Medical Products Administration (NMPA), general cosmetic product filing information; with English translation, Jul. 7, 2015, 4 pages; https://hzoba.nmpa.gov.cn/gccx/.
International Search Report and Written Opinion mailed Apr. 9, 2020 for Application No. PCT/EP2020/050215, 10 pages.
Molina, et al: "Glico Cosmetologia: A Polisaccaride ramnosilato antinfiammatorio"; Glyco-cosmetology: Anti-inflammatory rhamnosilylated polysaccharides, Cosmetic Technology; Jan. 1, 2004; vol. 7(2), pp. 29-33, with English translation.
Prohic, et al: "The Prevalence and Species Composition of Malassezia yeasts in Patients with Clinically Suspected Onychomycosis", Med. Arh; Apr. 2015; vol. 69(2), pp. 81-84.
Westerberg, et al: "Onychomycosis: Current Trends in Diagnosis and Treatment", American Family Physician; Dec. 1, 2013; vol. 88(11), pp. 762-770.

* cited by examiner

*Primary Examiner* — Pancham Bakshi
(74) *Attorney, Agent, or Firm* — Squire Patton Boggs (US )LLP

(57) ABSTRACT

It relates to a combination comprising a) rhamnose or a rhamnose-rich polysaccharide; b) a film-forming agent; and c) one or more further active agents selected from: i) a hyaluronic acid derivative selected from the group consisting of hyaluronic acid, a pharmaceutically or cosmetically acceptable salt thereof, and a cationized hyaluronic acid, ii) a silanol compound, and iii) an extract of *Pistacia lentiscus*; for use in the treatment and/or prevention of fungal infections in human beings. It also relates to this combination per se, and to pharmaceutical or cosmetic topical nail composition containing it.

19 Claims, 1 Drawing Sheet

NAIL COMPOSITIONS HAVING ANTIFUNGAL PROPERTIES

CROSS-REFERENCE

This application is a 35 USC 371 national phase filing of PCT/EP2020/050215 filed on Jan. 7, 2020, which claims the benefit of and priority to European Patent Application 19382010.7 filed on Jan. 8, 2019, both applications are incorporated herein by reference in their entirety.

TECHNICAL FIELD

The present invention relates to the use of combinations of at least two active agents, being one of them rhamnose or a rhamnose-rich polysaccharide, in the treatment and/or prevention of fungal infections in human beings. It also relates to these combinations containing rhamnose or a rhamnose-rich polysaccharide, and to pharmaceutical and cosmetic topical nail compositions containing them.

BACKGROUND ART

Nails, including fingernails and toenails, are mainly composed of keratin. Keratins are fibrous proteins involved in the mechanical stability and integrity of epithelial cells against mechanical and non-mechanical stress, which may cause cell death. Keratins are divided into two types: "soft" keratins, which can be found in skin, and "hard" keratins which can be found in hair fibers and nails. In the nails, keratins are embedded in a matrix consisting of proteins and keratin (keratin-associated proteins, KAPs). KAPs are essential for the formation of rigid and resistant nails.

Nail disorders affect people of all ages and are a common cause of consultation with a dermatologist. One of the most prevalent nail problems is the splitting or cracking of the nail layers, which is also referred to as brittle nails. Brittle nails are heterogeneous abnormalities characterized by weakness, inelasticity, and overall fragility of the nail plate, and may be caused by internal and/or external factors.

Brittle nails are not only an aesthetic problem, especially when affect fingernails, which may significantly impair a person's everyday activities, but may also lead to complications, such as nail infections.

Onychomycosis is a fungal infection of the nail, whose symptoms may include yellow, red, or brown nail discoloration, thickening of the nail (sometimes the entire nail plate has a rough appearance), separation of the nail from the nail bed, and brittle nails.

Onychomycosis is caused by dermatophytes (predominantly *Trichophyton rubrum* and *Trichophyton mentagrophytes* but also *Epidermophyton floccosum*, *Microsporum* spp, *Trichophyton violaceum*, *Trichophyton verrucosum*, *Trichophyton krajdenii*, *Trichophyton interdigitale* and *Arthroderma* spp), non-dermatophyte molds (NDMs) (such as *Scopulariopsis brevicaulis*, *Aspergillus* spp, *Acremonium*, *Fusarium* spp, *Alternaria* alternate, and *Neoscytalidium*), and yeasts (e.g. *Candida* spp). Some cases of onychomycosis involving *Malassezia* species (such as *Malassezia furfur*) or *Candida* species (such as *Candida albicans*) have also been reported (Med. Arh. 2015 April; 69(2): 81-84, Am Fam Physician. 2013 Dec. 1; 88(11):762-770). Infection by *Malassezia* yeasts is probably caused by subungual colonization by members of the cutaneous microbiota. Infections by *Malassezia* or *Candida* may be treated e.g. by topical therapy with cyclopiroxolamine or oral ketoconazole. Generally, topical therapy presents some advantages over oral treatment mainly because of the elimination of systemic adverse effects and drug interactions due to the local treatment.

Despite the existence of the above treatments, they are often not fully satisfactory because of lack of efficacy, intrinsic toxicity or other side-effects that limit their applicability. Besides, the frequent use of the antifungals in these pathologies could produce an increase in fungal resistance to these drugs.

Therefore, there is still a need for nail compositions that improve hardness and strength of the nails, thus preventing nail fragility, while having antifungal properties.

SUMMARY OF INVENTION

The inventors have developed a combination of at least two active ingredients, being one of them rhamnose or a rhamnose-rich polysaccharide, which shows antifungal activity. Without being bound to theory it is thought that the antifungal activity is due to the presence of this component. In particular, in the examples below it is demonstrated that compositions containing this active agent have activity against a variety of fungal species such as *Malassezia* species, *Candida* species, and *Trichophyton* species. To the knowledge of the inventors, rhamnose or the rhamnose-rich polysaccharides disclosed herein have only been described in this type of combinations as anti-inflammatory agents.

Apart from rhamnose or the rhamnose-rich polysaccharide, the combination of the invention also contains at least a film-forming agent, and a further active agent selected from a hyaluronic acid derivative, a silanol compound, and an extract of *Pistacia lentiscus*. The combination of the invention is especially suitable for enhancing nail health, nail hardness, nail flexibility and preventing and treat nail fragility.

Therefore, a first aspect of the invention relates to a combination comprising:
 a) rhamnose or a rhamnose-rich polysaccharide, wherein the rhamnose-rich polysaccharide comprises rhamnose in an amount equal or higher than 30% w/w;
 b) a film-forming agent; and
 c) one or more further active agents selected from:
  i) a hyaluronic acid derivative selected from the group consisting of hyaluronic acid, a pharmaceutically or cosmetically acceptable salt thereof, and a cationized hyaluronic acid, wherein the cationized hyaluronic acid is a hyaluronic acid wherein the hydrogen atom of at least one of the hydroxylic groups or the carboxylic group is replaced by a moiety of formula (III):

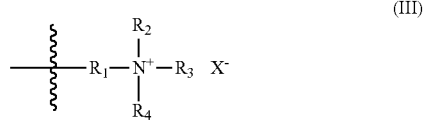

wherein each of $R_1$-$R_4$ independently represents a linear or branched ($C_1$-$C_6$)alkyl group optionally substituted with one or more hydroxyl groups, and X is a halogen ion;
  ii) a silanol compound, and
  iii) an extract of *Pistacia lentiscus*.

The combination of the invention may be formulated together with further suitable excipients as a pharmaceutical or cosmetic composition to be conveniently administered topically to the nails. Accordingly, a further aspect of the invention relates to a pharmaceutical or cosmetic topical nail composition which comprises the combination as defined above, together with one or more further pharmaceutically or cosmetically acceptable excipients or carriers.

As mentioned above, the combination of the invention, thanks to the presence of rhamnose or the rhamnose-rich polysaccharide, is active against fungal infections. Therefore, a further aspect of the invention relates to the use of the combination comprising rhamnose or a rhamnose-rich polysaccharide, or the pharmaceutical or cosmetic topical nail composition as defined above, as antifungal product.

A further aspect of the invention relates to a combination comprising rhamnose or a rhamnose-rich polysaccharide or the pharmaceutical or cosmetic topical nail composition as defined above for use in the treatment and/or prevention of fungal infections in human beings.

This aspect may also be formulated as the use of the combination comprising rhamnose or a rhamnose-rich polysaccharide as defined above for the manufacture of a medicament or cosmetic composition for the treatment and/or prevention of fungal infections in human beings.

It also forms part of the invention a method for the treatment and/or prevention of fungal infections in human beings, comprising administering an effective amount of the combination comprising rhamnose or a rhamnose-rich polysaccharide as defined above, and one or more pharmaceutically or cosmetically acceptable excipients or carriers, in a subject in need thereof, including a human.

DETAILED DESCRIPTION OF THE INVENTION

Figure 1:
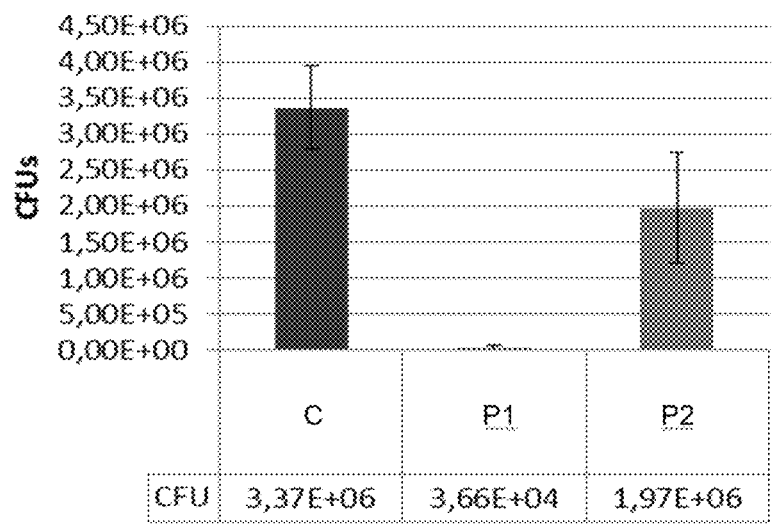
FIG. 1 shows an ex-vivo determination of the antifungal activity against *Malassezia furfur* in human skin explants of piroctone olamine (P1), and the composition of example 2 (P2).

All terms as used herein in this application, unless otherwise stated, shall be understood in their ordinary meaning as known in the art. Other more specific definitions for certain terms as used in the present application are as set forth below and are intended to apply throughout the description and claims.

The term "about" or "around" as used herein refers to a range of values±10% of a specified value. For example, the expression "about 10" or "around 10" includes ±10% of 10, i.e. from 9 to 11.

Unless otherwise stated, all percentages mentioned herein regarding the components of the composition are expressed in weight with respect to the total weight of the composition, provided that the sum of the amounts of the components is equal to 100%.

As mentioned above, the invention relates to a combination of at least two active agents comprising:
a) rhamnose or a rhamnose-rich polysaccharide, wherein the rhamnose-rich polysaccharide comprises rhamnose in an amount equal or higher than 30% w/w;
b) a film-forming agent; and
c) one or more further active agents selected from:
i) a hyaluronic acid derivative selected from the group consisting of hyaluronic acid, a pharmaceutically or cosmetically acceptable salt thereof, and a cationized hyaluronic acid, wherein the cationized hyaluronic acid is a hyaluronic acid wherein the hydrogen atom of at least one of the hydroxylic groups or the carboxylic group is replaced by a moiety of formula (III):

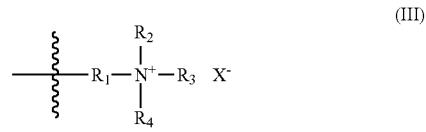

wherein each of $R_1$-$R_4$ independently represents a linear or branched ($C_1$-$C_6$)alkyl group optionally substituted with one or more hydroxyl groups, and X is a halogen ion;
i) a silanol compound, and
ii) an extract of *Pistacia lentiscus*.

In one embodiment, optionally in combination with one or more features of the various embodiments described above or below, the weight ratio between the rhamnose or the rhamnose-rich polysaccharide; and the film-forming agent is from 1:3 to 1:9, more particularly from 1:4 to 1:7.

In another embodiment, optionally in combination with one or more features of the various embodiments described above or below, the combination of the invention comprises or consists of rhamnose or a rhamnose-rich polysaccharide; a film-forming agent; and a hyaluronic acid derivative as defined above. More particularly, the weight ratio between the rhamnose-rich polysaccharide; and the hyaluronic acid derivative is from 1:2 to 1:6, more particularly from 1:3 to 1:5.

In another embodiment, optionally in combination with one or more features of the various embodiments described above or below, the combination of the invention comprises or consists of rhamnose or a rhamnose-rich polysaccharide; a film-forming agent; and a silanol compound. More particularly, the weight ratio between the rhamnose-rich polysaccharide; and the silanol compound is from 1:3 to 1:7, more particularly from 1:4 to 1:6.

In another embodiment, optionally in combination with one or more features of the various embodiments described above or below, the combination of the invention comprises or consists of rhamnose or a rhamnose-rich polysaccharide; a film-forming agent; and an extract of *Pistacia lentiscus*. More particularly, the weight ratio between the rhamnose-rich polysaccharide; and the extract is from 1:3 to 3:1, more particularly from 1:2 to 2:1.

In another embodiment, optionally in combination with one or more features of the various embodiments described above or below, the combination of the invention comprises or consists of rhamnose or a rhamnose-rich polysaccharide; a film-forming agent; a silanol compound; and a hyaluronic acid derivative as defined above.

In another embodiment, optionally in combination with one or more features of the various embodiments described above or below, the combination of the invention comprises or consists of rhamnose or a rhamnose-rich polysaccharide; a film-forming agent; an extract of *Pistacia lentiscus*; and a hyaluronic acid derivative.

In another embodiment, optionally in combination with one or more features of the various embodiments described above or below, the combination of the invention comprises or consists of rhamnose or a rhamnose-rich polysaccharide; a film-forming agent; a silanol compound; and an extract of *Pistacia lentiscus*.

In another embodiment, optionally in combination with one or more features of the various embodiments described above or below, the combination of the invention comprises or consists of rhamnose or a rhamnose-rich polysaccharide; a film-forming agent; a silanol compound; an extract of *Pistacia lentiscus*; and a hyaluronic acid derivative.

Rhamnose and Rhamnose-Rich Polysaccharides

As mentioned above, the inventors have found that rhamnose or a rhamnose-rich polysaccharide as defined herein show antifungal activity. Additionally, rhamnose or a rhamnose-rich polysaccharide may also be useful for their soothing, moisturizing, and/or restructuring properties of the nails.

Rhamnose is a naturally occurring deoxy sugar that occurs in nature in its L-form as L-rhamnose (6-deoxy-L-mannose). In one embodiment, optionally in combination with one or more features of the various embodiments described above or below, the rhamnose is L-rhamnose.

In another embodiment, optionally in combination with one or more features of the various embodiments described above or below, the combination of the invention comprises a rhamnose-rich polysaccharide. More particularly, the rhamnose-rich polysaccharide comprises rhamnose, more particularly L-rhamnose, in an amount equal to or higher than 30% w/w, more particularly equal to or higher than 40% w/w. Even more particularly, the rhamnose-rich polysaccharide comprises rhamnose in an amount from 40% to 60%, more particularly from 45 to 55%, and even more particularly about 50% w/w.

In another embodiment, optionally in combination with one or more features of the various embodiments described above or below, the rhamnose-rich polysaccharide comprises a repeating unit of formula (I)

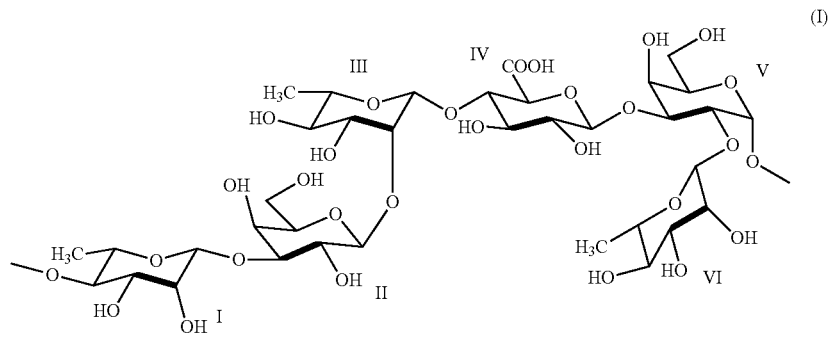

(I)

The above repeating unit of formula (I) is formed from units of rhamnose (I, III, VI), galactose (II, V) and glucuronic acid (IV). Thus, about 50% w/w of the polysaccharide is rhamnose.

In another embodiment, optionally in combination with one or more features of the various embodiments described above or below, the rhamnose-rich polysaccharide has a molecular weight from 45000 to 55000 g/mol, more particularly from 47000 to 52000 g/mol, even more particularly from 49000 to 51000 g/mol, and even more particularly about 50000 g/mol.

For the purposes of the present invention, the term "molecular weight" refers to the weight average molecular weight (Mw). Said molecular weight can be calculated by methods well known in the art such as viscometry, ultrafiltration vapor pressure and size exclusion chromatography (GPC/SEC).

In one embodiment, optionally in combination with one or more features of the various embodiments described above or below, the rhamnose-rich polysaccharide forms part of an aqueous solution and is present in the solution in an amount from 1 to 4% w/w, more particularly in an amount about 2.5% w/w.

In another embodiment, optionally in combination with one or more features of the various embodiments described above or below, the aqueous solution containing the rhamnose polysaccharide corresponds to the INCI designation Biosaccharide gum-2 (CAS Registry Number 758716-52-81). More particularly, it is in the form of an aqueous solution containing the polysaccharide having the repeating unit of formula (I) as described above in an amount of about 2.5% w/w; wherein the polysaccharide has about 50000 g/mol, contains L-rhamnose, D-Galactose and glucuronic acid.

Film-Forming Agents

The term "film-forming agent" as used herein refers to a polymer that allows the formation of a film on a substrate, such as the nails, to which it is applied. When the solvent is present in the composition, the film may be formed for example after the solvent is evaporated or absorbed into the substrate. The film-forming agent generally imparts hardness, toughness, and resistance to abrasion.

The film-forming polymer may be a homopolymer, a copolymer (including linear, block, branched, graft, comb, and star copolymers), or mixture thereof. It may be a nonionic, ionic (anionic or cationic), and amphoteric (including zwitterionic) polymer.

Non-limiting examples of film-forming agent include polyacryls, such as polyacrylates, polyacrylics, and polyacrylamides; polymethacrylics, such as polymethacrylates, polymethacrylics, and polymethacrylamides; polyurethanes; and polyvinyls.

In one embodiment, optionally in combination with one or more features of the various embodiments described above or below, the film-forming agent is selected from the group consisting of acrylate polymers; cellulose polymers, such as nitrocellulose, methyl cellulose, ethyl cellulose, and cellulose acetates; polyvinyl acetate, and mixtures thereof.

The term "acrylate polymer" as used herein refers to any molecule comprising two or more acrylate monomers linked covalently via the vinyl groups. Acrylate monomers are based on the structure of acrylic acid, which consists of a vinyl group and a carboxylic acid ester terminus. Other typical acrylate monomers are derivatives of acrylic acid, such as methyl methacrylate in which one vinyl hydrogen and the carboxylic acid hydrogen are both replaced by methyl groups, and acrylonitrile in which the carboxylic acid group is replaced by the corresponding nitrile group. Acrylate polymers are also known as acrylics or polyacrylates. The term acrylate polymer includes homopolymers and copolymers of alkyl acrylates, in which e.g. the alkyl group contains from one to eight carbon atoms, and copolymers thereof with, for example, another material such as acrylic acid, methacrylic acid, alkyl methacrylate esters, wherein e.g. the alkyl groups contain 2 to 4 carbon atoms, vinyl acetate, acrylonitrile, and styrene.

In another embodiment, optionally in combination with one or more features of the various embodiments described above or below, the film-forming agent is an acrylate polymer. More particularly, an acrylate polymer selected from the group consisting of acrylic acid, acrylic acid esters, methacrylic acid, methacrylic acid esters, polyacrylic acid, Methacrylic Acid/Ethyl Acrylate copolymer, carbomer, carboxyvinyl polymer, carboxypolymethylene polymer, polyacrylate elastomers, polyacrylates, polyacrylate copolymer, polyacrylate crosspolymers, acrylates/alkyl acrylate crosspolymer, AMP-acrylates/Allyl Methacrylate Copolymer, acrylates/acrylamide copolymer, acrylic acid/alkyl methacrylate copolymer, silicone/acrylates copolymer, acrylates/polyurethane copolymer, and combinations thereof.

In another embodiment, optionally in combination with one or more features of the various embodiments described above or below, the film-forming agent, in particular the acrylate polymer, forms part of an aqueous solution, which may contain glycols such as propylene glycol, and is present in the solution in an amount from 25 to 35% w/w, more particularly in an amount about 29% w/w.

In another embodiment, optionally in combination with one or more features of the various embodiments described above or below, the film-forming agent is Acrylates copolymer. More particularly, it forms part of an aqueous solution, which may contain glycols such as propylene glycol, and is present in the solution in an amount from 25 to 35% w/w, more particularly in an amount about 29% w/w.

The term "acrylates copolymer" as used herein corresponds to the INCI Name designation. It is also known under the following CAS Registry Numbers: 25133-97-5, 25035-69-2, 25212-88-8). Acrylates copolymer refers to a copolymer of two or more monomers selected from the group consisting of acrylic acid, methacrylic acid, and esters of any of them, including $(C_1-C_{10})$alkyl esters, such as for example and without limitation, methyl, ethyl, butyl, propyl, or octyl esters.

Hyaluronic Acid Derivative

Hyaluronic acid (HA, CAS Registry Number: 9004-61-9) is a naturally occurring non-sulfated anionic glycosaminoglycan which contains several repeating disaccharide units of N-acetyl-D-glucosamine (GlcNac) and D-glucuronic acid (GlcUA).

The hyaluronic acid derivative plays an important role in maintaining the nail structure and in retaining nail moisture/hydration, lubrication, and flexibility. It also promotes cuticle recovery.

The hyaluronic acid derivative of the invention is selected from the group consisting of hyaluronic acid, a pharmaceutically or cosmetically acceptable salt thereof, and a cationized hyaluronic acid.

In one embodiment, optionally in combination with one or more features of the various embodiments described above or below, the hyaluronic acid derivative is hyaluronic acid, more particularly from 500 kDa to 800 kDa.

Pharmaceutical or cosmetically acceptable salts of hyaluronic acid may also be part of the combination active ingredients of the invention. There is no limitation on the type of hyaluronic acid salt that can be used, as long as they are pharmaceutically or cosmetically acceptable when used for therapeutic or cosmetic purposes. The hyaluronic acid and its corresponding salt may differ in some physical properties, but they are equivalent for the purposes of the present invention.

The term "pharmaceutically acceptable salt" refers to the salt appropriate for use in pharmaceutical technology for the preparation of compositions for medical use and, the term "cosmetically acceptable salt" refers to the appropriate salt for use in contact with human skin, in particular nails, without toxicity, incompatibility, instability, inappropriate allergic response, among others. In particular, the term "pharmaceutical or cosmetically acceptable salt" encompasses commonly used salts such as, for example, alkali metal salts. The preparation of pharmaceutically acceptable salts of hyaluronic acid can be carried out by methods known in the art. Non-limiting examples of pharmaceutically or cosmetically acceptable salts of hyaluronic acid suitable for the present invention include inorganic salts such as sodium hyaluronate, magnesium hyaluronate, potassium hyaluronate, zinc hyaluronate and cobalt hyaluronate, as well as organic salts such as tetrabutylammonium hyaluronate.

In one embodiment, optionally in combination with one or more features of the various embodiments described above or below, the hyaluronic acid derivative is a cationized hyaluronic acid. The cationized hyaluronic acid has the advantage with respect to the non-cationized hyaluronic acid (i.e. hyaluronic acid) that it has an improved penetration into the nail plate and remains for a longer period of time in the treated area.

For the purposes of the present invention, a cationized hyaluronic acid refers to a hyaluronic acid, wherein the hydrogen atom of at least one of the hydroxylic groups (OH) or the carboxylic group (COOH) is replaced with a moiety of the formula (III):

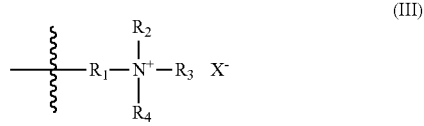

wherein each of $R_1$-$R_4$ independently represents a linear or branched $(C_1-C_6)$alkyl group optionally substituted with one or more hydroxyl groups, and X is a halogen ion such as a fluorine ion, a bromine ion, chlorine ion, and an iodine ion.

In one embodiment, optionally in combination with one or more features of the various embodiments described above or below, the cationized hyaluronic acid is a hyaluronic acid wherein the hydrogen atom of the carboxylic group (COOH) is replaced with a moiety of the formula (III) as defined above.

In another embodiment, optionally in combination with one or more features of the various embodiments described above or below, the cationized hyaluronic acid has a degree of substitution from 0.1 to 0.6, more preferably from 0.15 to 0.35.

The term "degree of substitution" or degree of cationization of the cationized hyaluronic acid as used herein refers to the number of quaternary ammonium groups for each repetitive unit of hyaluronic acid (consisting of the dimer GlcNAc-GlcUA). The degree of substitution can be measured using $^1$H nuclear magnetic resonance spectroscopy.

In another embodiment, optionally in combination with one or more features of the various embodiments described above or below, the cationized hyaluronic acid has the formula (II):

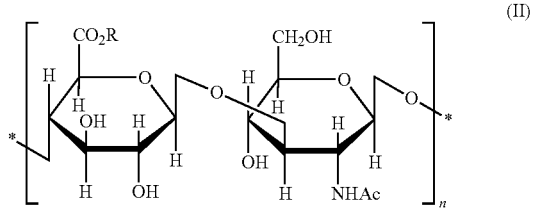

(II)

wherein R is a moiety of the formula (III) as previously defined.

In a more particular embodiment, optionally in combination with one or more features of the various embodiments described above or below, the cationized hyaluronic acid has the formula (II), and the moiety of the formula (III) has the formula (IIIa):

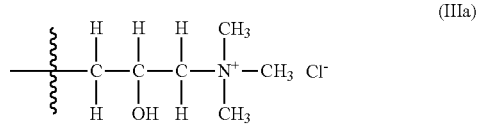

(IIIa)

In another embodiment, optionally in combination with one or more features of the various embodiments described above or below, the cationized hyaluronic acid corresponds to the INCI Name designation Hydroxypropyltrimonium Hyaluronate (CAS Registry Number: 999999-97-1).

Silanol Compounds

For the purposes of the invention, the term "silanol compound" refers to a compound having one or more Si—(OH)$_x$ moieties wherein x is 1 (monohydroxysilanes), 2 (dihydroxy-silanes or silanediols), or 3 (trihydroxysilanes or silanetriols).

The silanol compounds improve the elasticity of the skin and reduce the appearance of imperfections. It also regenerates damaged collagen fibers and intervenes in the formation of new fibers, thereby promoting healthy nail growth.

Non-limiting examples of silanol compounds include (indicated according to their INCI names): Methylsilanol Mannuronate, Silanetriol Arginate, Ascorbyl Methylsilanol Pectinate, Siloxanetriol Alginate, Silanediol Salicylate, Dimethylsilanol Hyaluronate, Silanetriol, Silanetriol Trehalose Ether, Silanetriol Glutamate, Silanetriol Lysinate, Methylsilanol Hydroxyproline Aspartate, Sodium Lactate Methylsilanol, Dioleyl Tocopheryl Methylsilanol, Polysilicone-3, Dimethyl oxobenzo dioxasilane, Copper PCA Methylsilanol, Methylsilanol Carboxymethyl Theophylline Alginate, Methylsilanol Acetyltyrosine, Acefylline Methylsilanol Mannuronate, and the like.

In one embodiment, optionally in combination with one or more features of the various embodiments described above or below, the silanol compound is a silanediol or a silanetriol. More particularly, the silanol compound is silanediol salicylate.

In another embodiment, optionally in combination with one or more features of the various embodiments described above or below, the silanediol salicylate forms part of a glycolic solution, more particularly a butylenglycol solution, and is present in the solution in an amount from 18 to 26% w/w, more particularly in an amount about 24% w/w.

The term "glycol" refers herein to an organic compound having two hydroxyl (—OH) groups are attached to different carbon atoms. Non-limiting examples of glycols include ethylene glycol, propylene glycol (1,2-propanediol), butylenglycol (including 1,2-butanediol, 1,3-butanediol, 1,4-butanediol, and 2,3-butanediol).

In another embodiment, optionally in combination with one or more features of the various embodiments described above or below, the silanediol salicylate is commercially available as a glycolic solution of dimethylsilanediol salicylate which corresponds to the INCI designation Silanediol Salicylate (and) Butylene Glycol (and) Triethanolamine (CAS Registry Numbers: 2-[(Hydroxydimethylsilyl)oxy] benzoic acid (187939-06-6), 1,3-Butanediol (107-88-0), and Triethanolamine (102-71-6)).

Extract of *Pistacia lentiscus*

The term "extract of *Pistacia lentiscus*" is used herein to refer to concentrated preparations obtained using extraction procedures from *Pistacia lentiscus* (mastic) by the appropriate means.

The extract of *Pistacia lentiscus* increases the expression of hard keratins and KAPs in the nails as well as their thickness.

The *Pistacia lentiscus* L. is a small evergreen shrub native to the Mediterranean countries which is cultivated for its aromatic resin. The variety *Pistacia lentiscus* L. var. Chia is cultivated on Chios island, Greece, and yields the resin known as mastic gum, which is obtained by shallow incisions of the bark or the trunk and main branches. The appropriate means to extract the active principles include, for example, extraction with supercritical fluids. (such as supercritical CO$_2$).

The extract of *Pistacia lentiscus* contains several components including a natural polymer (cis-1,4-poly-β-myrcene), triterpenes (tetracyclic euphane- and dammarane skeleton type and of the pentacyclic oleanane and lupane skeleton type, such as mastic acid, isomastic acid, oleanolic acid, tirucallol), monoterpene hydrocarbons, 20% oxygenated monoterpenes and sesquiterpenes; polyphenols (tyrosol, p-hydroxy-benzoic acid, p-hydroxy-phenyl acetic acid, vanillic acid and gallic acid), and phytosterols.

In one embodiment, optionally in combination with one or more features of the various embodiments described above or below, the extract of *Pistacia lentiscus* is a concentrate obtained by supercritical CO$_2$ extraction from crystal drops collected on *Pistacia lentiscus*.

In another embodiment, optionally in combination with one or more features of the various embodiments described above or below, the extract of *Pistacia lentiscus* forms part of an oil solution, more particularly a caprylic/capric triglyceride solution, and is present in the solution in an amount from 15 to 25% w/w, more particularly in an amount about 20% w/w.

In another embodiment, optionally in combination with one or more features of the various embodiments described above or below, the extract of *Pistacia lentiscus* corresponds to the INCI designation Caprylic/capric triglyceride (and) *Pistacia lentiscus* (Mastic) Gum (CAS Registry Numbers: Caprylic/capric triglyceride (73398-61-5), and *Pistacia lentiscus* (Mastic) Gum (61789-92-2)).

Pharmaceutical and Cosmetic Compositions

As mentioned above it also forms part of the invention a pharmaceutical or cosmetic topical nail composition which comprises an effective amount of the combination as defined above, together with one or more pharmaceutically or cosmetically acceptable excipients or carriers.

In one embodiment, optionally in combination with one or more features of the various embodiments described above or below, the pharmaceutical or cosmetic topical nail composition consists of the combination as defined above and one or more pharmaceutically or cosmetically acceptable excipients or carriers. In this embodiment, the composition does not include any active agents apart from rhamnose or a rhamnose-rich polysaccharide and one or more further active agents selected from: hyaluronic acid derivative as defined above, a silanol compound, and an extract of *Pistacia lentiscus*.

The expression "pharmaceutically acceptable excipients or carriers" means that the excipients or carriers are suitable for the preparation of compositions for pharmaceutical or medical uses in humans and animals. Each component must be pharmaceutically acceptable in the sense of being compatible with the other ingredients of the pharmaceutical composition. It must also be suitable for use in contact with tissues or organs of humans and animals without excessive toxicity, irritation, allergic response, immunogenicity or other problems or complications consistent with a reasonable risk/benefit relationship.

The expression "cosmetically acceptable excipients or carriers" means that the excipients or carriers are suitable for the preparation of compositions for cosmetic use. Each component must be cosmetically acceptable in the sense of being compatible with the other ingredients of the cosmetic composition. It must also be suitable for use in contact with tissues or organs of humans and animals without excessive toxicity, irritation, allergic response, immunogenicity or other problems or complications consistent with a reasonable risk/benefit relationship.

The expression "effective amount" as used herein, relates to the amount of product that provides the cosmetic or therapeutic desired effect after its application. The effective amount that provides a therapeutic effect (also cited here as therapeutically effective amount) is the amount of a compound that, when administered, is sufficient to prevent the development of, or to relieve to some degree one or more of the symptoms of the disease to which it is directed. The particular dose of compound administered according to this invention may vary according to the particular conditions surrounding the case, including the administered compound, the route and frequency of administration, age, condition of the patient, nature or severity of the condition, disorder or condition to be treated or prevented and similar considerations.

In one embodiment, optionally in combination with one or more features of the various embodiments described above or below, the topical nail composition is a pharmaceutical composition. In another particular embodiment, optionally in combination with one or more features of the various embodiments described above or below, the composition is a cosmetic composition.

In one particular embodiment, optionally in combination with one or more features of the various embodiments described above or below, in the pharmaceutical or cosmetic composition previously described either rhamnose or alternatively, the rhamnose-rich polysaccharide is the only saccharide present in the composition.

In another embodiment, optionally in combination with one or more features of the various embodiments described above or below, the pharmaceutical or cosmetic topical nail composition comprises rhamnose or a rhamnose-rich polysaccharide; a film-forming agent; and a hyaluronic acid derivative as defined above.

In another embodiment, optionally in combination with one or more features of the various embodiments described above or below, the pharmaceutical or cosmetic topical nail composition consists of:
a) rhamnose or a rhamnose-rich polysaccharide and a hyaluronic acid derivative as defined above as the only active agents;
b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide; a film-forming agent; and a silanol compound.

In another embodiment, optionally in combination with one or more features of the various embodiments described above or below, the pharmaceutical or cosmetic topical nail composition consists of:
a) rhamnose or a rhamnose-rich polysaccharide and a silanol compound as the only active agents;
b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide; a film-forming agent; and an extract of *Pistacia lentiscus*.

In another embodiment, optionally in combination with one or more features of the various embodiments described above or below, the pharmaceutical or cosmetic topical nail composition consists of:
a) rhamnose or a rhamnose-rich polysaccharide and an extract of *Pistacia lentiscus* as the only active agents;
b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide; a film-forming agent; a silanol compound; and a hyaluronic acid derivative as defined above.

In another embodiment, optionally in combination with one or more features of the various embodiments described above or below, the pharmaceutical or cosmetic topical nail composition consists of:
a) rhamnose or a rhamnose-rich polysaccharide; a hyaluronic acid derivative as defined above; and a silanol compound; as the only active agents;

b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide; a film-forming agent; an extract of *Pistacia lentiscus*; and a hyaluronic acid derivative as defined above.

In another embodiment, optionally in combination with one or more features of the various embodiments described above or below, the pharmaceutical or cosmetic topical nail composition consists of:
a) rhamnose or a rhamnose-rich polysaccharide; a hyaluronic acid derivative as defined above; and an extract of *Pistacia lentiscus*; as the only active agents;
b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide; a film-forming agent; a silanol compound; and an extract of *Pistacia lentiscus*.

In another embodiment, optionally in combination with one or more features of the various embodiments described above or below, the pharmaceutical or cosmetic topical nail composition consists of:
a) rhamnose or a rhamnose-rich polysaccharide; a silanol compound; and an extract of *Pistacia lentiscus*; as the only active agents;
b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide; a film-forming agent; a silanol compound; an extract of *Pistacia lentiscus*; and a hyaluronic acid derivative as defined above.

In another embodiment, optionally in combination with one or more features of the various embodiments described above or below, the pharmaceutical or cosmetic topical nail composition consists of:
a) rhamnose or a rhamnose-rich polysaccharide; a hyaluronic acid derivative as defined above; a silanol compound; and an extract of *Pistacia lentiscus*; as the only active agents;
b) a film-forming agent; and
c) one or more further pharmaceutically or cosmetically acceptable excipients or carriers.

In another embodiment, optionally in combination with one or more features of the various embodiments described above or below, the pharmaceutical or cosmetic topical nail composition comprises rhamnose or a rhamnose-rich polysaccharide in an amount from 0.02 to 0.1 wt %, more particularly from 0.03 to 0.07 wt %, with respect to the weight of the total composition.

In a more particular embodiment, the rhamnose-rich polysaccharide forms part of an aqueous solution, wherein the solution contains from 1 to 4% w/w, more particularly about 2.5% w/w of the rhamnose-rich polysaccharide, and the aqueous solution is present in the composition in an amount from 1 to 3 wt %, more particularly from 1.5 to 2.5 wt %, with respect to the weight of the total composition.

In another embodiment, optionally in combination with one or more features of the various embodiments described above or below, the pharmaceutical or cosmetic topical nail composition comprises a film-forming agent in an amount from 0.1 to 1 wt %, more particularly from 0.1 to 0.5 wt %, with respect to the weight of the total composition.

In a more particular embodiment, the film-forming agent forms part of an aqueous solution, wherein the solution contains from 25 to 35% w/w, and the aqueous solution is present in the composition in an amount from 0.5 to 2 wt %, more particularly from 0.8 to 1.5 wt %, with respect to the weight of the total composition.

In another embodiment, optionally in combination with one or more features of the various embodiments described above or below, the pharmaceutical or cosmetic topical nail composition comprises hyaluronic acid derivative as defined above in an amount from 0.05 to 1 wt %, more particularly from 0.08 to 0.5 wt %, with respect to the weight of the total composition.

In another embodiment, optionally in combination with one or more features of the various embodiments described above or below, the pharmaceutical or cosmetic topical nail composition comprises a silanol compound in an amount from 0.1 to 0.8 wt %, more particularly from 0.15 to 0.5 wt %, with respect to the weight of the total composition.

In a more particular embodiment, the silanol compound forms part of an aqueous solution, wherein the solution contains from 18 to 26% w/w, more particularly about 24% w/w of the silanol compound, and the aqueous solution is present in the composition in an amount from 0.5 to 2 wt %, more particularly from 0.8 to 1.5 wt %, with respect to the weight of the total composition.

In another embodiment, optionally in combination with one or more features of the various embodiments described above or below, the pharmaceutical or cosmetic topical nail composition comprises an extract of *Pistacia lentiscus* in an amount from 0.01 to 0.3 wt %, more particularly from 0.02 to 0.1 wt %, with respect to the weight of the total composition.

In a more particular embodiment, the extract of *Pistacia lentiscus* forms part of an oil solution, more particularly a caprylic/capric triglyceride solution, wherein the solution contains from 15 to 25% w/w, more particularly about 20% w/w of the extract, and the oil solution is present in the composition in an amount from 0.1 to 1 wt %, more particularly from 0.1 to 0.5 wt %, with respect to the weight of the total composition.

Generally, topical nail formulations include nail polish (also known as varnish, lacquers or enamels) sprays, mousses, gels, solutions, serums, oils, creams, lotions, and the like, wherein the combination of the invention, together or separately, is dispersed or dissolved in suitable excipients.

The election of the type of formulation will depend upon different factors, including the nature of the active compounds, and the condition to be treated. The excipients or carriers used have affinity for the nails, are well tolerated, are stable, and are used in an amount suitable to provide the desired consistency and ease of application. The appropriate excipients and/or carriers, and their amounts, can readily be determined by those skilled in the art according to the type of formulation being prepared.

Examples of suitable carriers and excipients that may be used in nail compositions include gelling agents; moisturizers; humectants; emollients; pH adjusters; preservatives, such as phenoxyethanol; surfactants such as Tween and sodium lauryl sulfate, solvents; solubilizers; plasticizers; coloring agents, such as dyes, lakes, and pigments; suspending agents; opacifying agents, such as titanium dioxide or zinc oxide; UV absorbers such as benzophenones; and perfumes.

Gelling agents may be used to provide a gel consistency. Non-limiting examples of gelling agents include vinyl acetate copolymers, cellulose derivatives, polyvinyl pyrrolidone and carboxyvinyl copolymers.

Examples of humectants include, without limitation, glycerin, diglycerin, ethylhexylglycerin, pentylene glycol, polyethylene glycol, propylene glycol, butylene glycol, sorbitol, sucrose, or trehalose. Preferably, the humectant is selected group consisting of propylene glycol and butylene glycol, and their mixtures. Humectant may be present in the formulation in an amount from 0.1 to 2 wt % with respect to the total weight of the composition.

Examples of pH adjusters agents include, without limitation, monobasic sodium phosphate, dibasic sodium phosphate, benzoic acid, sodium citrate, triethanolamine, sodium hydroxide, lactic and citric acid, tromethamine, and the like. pH adjusters may be present in the formulation in an amount from 0.02 to 1 wt % with respect to the total weight of the composition.

Non-limiting examples of emollients include Caprylic/capric Triglyceride, C13-C14 isoparaffin, cyclohexasiloxane, cyclopentasiloxane, cetyl alcohol, isodecyl neopentanoate, almond oil, cetostearoyl alcohol, cetyl alcohol, cetyl esters wax, cottonseed oil, cyclomethicone, ethylene glycol palmitostearate, isopropyl myristate, isopropyl palmitate, lanolin, lecithin, light mineral oil, medium-chain triglycerides, mineral oil and lanolin alcohols, petrolatum, soybean oil stearyl alcohol, sunflower oil, xylitol and combinations thereof. Emollients may be present in the formulation in an amount from 0.1 to 1 wt % with respect to the total weight of the composition Solvents may facilitate to obtain a homogeneous formulation and provide appropriate viscosity. Non-limiting examples of solvents include ethanol, and water. Solvents may be present in the formulation in an amount from 30 to 97 wt % with respect to the total weight of the composition.

Non-limiting examples of solubilizers include Peg-40 hydrogenated castor oil, PEG-60 hydrogenated castor oil.

In one embodiment, optionally in combination with one or more features of the various embodiments described above or below, the pharmaceutical or cosmetic topical nail composition is a nail varnish. The nail varnish of the invention shows a proper viscosity and flow properties to be applied: it is in liquid form until applied to nails and has quick drying time (about 1-2 minutes).

In another embodiment, optionally in combination with one or more features of the various embodiments described above or below, the pharmaceutical or cosmetic topical nail composition comprises or consists of:
  a) rhamnose or a rhamnose-rich polysaccharide, wherein the rhamnose-rich polysaccharide comprises rhamnose in an amount equal or higher than 30% w/w;
  b) a film-forming agent; and
  c) one or more further active agents selected from:
    i) a hyaluronic acid derivative as defined above,
    ii) a silanol compound, and
    iii) an extract of *Pistacia lentiscus*.
together with one or more pharmaceutically or cosmetically acceptable excipients or carriers selected from solvents, emollients, pH adjusters, solubilizers, and humectants.

As mentioned above, the combination of the invention, thanks to the presence of rhamnose or the rhamnose-rich polysaccharide, is active against fungal infections. As shown in the examples below, rhamnose or a rhamnose-rich polysaccharide has activity against *Malassezia* species, *Candida* species, and *Trichophyton* species. Thus, rhamnose or a rhamnose-rich polysaccharide has the advantage that has a broad spectrum of activity since it is not only active against usual yeasts present in the nails but also active against yeasts that are less common in onychomycosis.

In one embodiment, optionally in combination with one or more features of the various embodiments described above or below, the antifungal infection is caused by *Malassezia* species. More particularly, the antifungal infection is caused by *Malassezia furfur*.

In another embodiment, optionally in combination with one or more features of the various embodiments described above or below, the antifungal infection is caused by *Candida* species. More particularly, the antifungal infection is caused by *Candida albicans*.

In another embodiment, optionally in combination with one or more features of the various embodiments described above or below, the antifungal infection is caused by *Trichophyton* species. More particularly, the antifungal infection is caused by *Trichophyton interdigitale*.

Non-limiting examples of diseases that can be treated and/or prevented include *pityriasis versicolor*, seborrheic dermatitis, dandruff and onychomycosis.

In one embodiment, optionally in combination with one or more features of the various embodiments described above or below, the antifungal infection is a nail antifungal infection, more particularly the nail antifungal infection is onychomycosis; and even more particularly onychomycosis caused by *Malassezia furfur, Candida albicans* or *Trichophyton interdigitale*. The term "onychomycosis" as used herein refers to a fungal infection of either the nail plate and/or the nail bed.

As mentioned above the combination of the invention and the compositions thereof as previously defined are especially suitable for enhancing nail health by improving or promoting one or more nail features such nail architecture, nail thickness, nail hardness, nail strength, nail moisture/hydration, nail lubrication, and nail flexibility thus preventing nail fragility. Accordingly, it also forms part of the invention the cosmetic use of the combination or the compositions as previously defined as nail care agent.

The term "cosmetic" is intended to denote a use intended, principally, to provide an aesthetic and/or comfort effect, in particular, to ameliorate the appearance of the nails. In the context of the present invention, when the composition of the invention is used as a nail care agent it does not intend to include any therapeutic use. The cosmetic use is addressed particularly to human beings that do not have any nail problems or diseases as e.g. onychomycosis or paronychia. When the combination of the invention is used for cosmetic purposes, it forms part of a topical cosmetic composition.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1

A nail topical product having the composition indicated in the table below was prepared according to a process comprising the following steps:

1. Base: Component 00 was added in the main container. The components (01), (03) and (04) were added in the main container until homogeneous solution. Component (02) was incorporated to the mixture by using a homogenizer (5000-6000 rpm).
2. Pre-phase 1: In an auxiliary vessel, component (010) was dissolved in component (011), and then component (012) was added.
3. Pre-phase 2: In an auxiliary vessel, component (021) was dissolved in component (020).
4. Pre-phase 3: In an auxiliary vessel, components (030) and (031) were mixed.
5. Pre-phase 1 was added to pre-phase 2, and the resulting mixture of pre-phases 01+02 was added to the previous base mixture. The pH of the mixture was adjusted with pre-phase 3.

| Component n° | INCI Name (Tradename) | Amount (% w/w) |
|---|---|---|
| 00 | Aqua | 78.76 |
| 01 | Aqua Biosaccharide gum-2 Phenoxyethanol (Rhamnosoft HP 1.5 p) | |
| 02 | Hydroxypropyltrimonium hyaluronate | |
| 03 | Aqua Acrylates copolymer Propylene glycol Benzyl alcohol Methylparaben (Avalure Ac 120 polymer) | |
| 04 | Alcohol denat. Aqua | |
| 010 | Caprylic/capric triglyceride *Pistacia lentiscus* gum | 12.75 |
| 011 | Peg-40 hydrogenated castor oil | |
| 012 | Alcohol denat. Aqua | |
| 020 | Alcohol denat. Aqua | 6.00 |
| 021 | Butylene glycol Silanediol salicylate Triethanolamine | |
| 030 | Aqua | 2.49 |
| 031 | Tromethamine | |
| | Total | 100.00 |

In the above composition, the weight ratio between the rhamnose-rich polysaccharide and the film-forming agent is about 1:5.8; the weight ratio between the rhamnose-rich polysaccharide and the hyaluronic acid derivative is about 1:4; the weight ratio between the rhamnose-rich polysaccharide and the silanol compound is about 1:5; and the weight ratio between the rhamnose-rich polysaccharide and the extract is about 1:1.

Example 2 and Comparative Example 3

Creams having the compositions indicated in the table below were prepared according to a process comprising the following steps:

1. Ingredients of phase A were mixed in the given order, with agitation after each addition until a homogeneous bulk was obtained. Then, the bulk was heated to 75-80° C.
2. Ingredients of phase B were weighed, heated to 75-80° C. and mixed until a homogeneous phase was obtained.
3. When both phases are at 75-80° C., phase B was slowly added to phase A and the mixture was homogenized.
4. The mixture obtained in step 3 was cooled down to 55° C., pH was adjusted with Sodium Hydroxide and the ingredients of phase C were added in the given order, with agitation after each addition until a homogeneous bulk is obtained.
5. The mixture obtained in step 4 was cooled down to 20-30° C.

| Phase | Ingredient INCI Name | Amount (% w/w) Example 2 | Amount (% w/w) Comparative example 3 |
|---|---|---|---|
| A | Aqua | q.s. | q.s. |
| | Glycerin | 7.00 | 7.00 |
| B | Isodecyl Neopentanoate Cetyl Alcohol Glyceryl Stearate Peg-100 Stearate | 7.00 | 7.00 |
| C | Laureth-7 Pentylene Glycol Polyacrylamide C13-14 Isoparaffin | 0.82 | 2.82 |
| | Biosaccharide Gum-2 | 0.05 | — |
| | Piroctone Olamine | — | 0.50 |
| D | Aqua and Sodium Hydroxide | q.s. | q.s. |
| | Total | 100.00 | 100.00 |

Efficacy, Compatibility and Acceptability Study on Nails

A study was carried out to assess the efficacy, as well as to check the compatibility and acceptability of the formulation of example 1. The test product was assessed in 30 subjects (age: 18-65 years old, gender: female) having brittle nails and weak nails with rough surface and/or tendency to break. The application of the product was carried out by the subject herself, once a day, for 28 or 84 consecutive days.

The efficacy of the product was assessed by instrumental measurements of the specific nails condition and characterization, with a Confocal Microscopy (Vivascope® 1500) system; and objectively and quantitatively; by instrumental measurements of the nail roughness with a Fringe projection system (Primos 3D®); by standardized photos obtained with standard illumination (one photography per subject of the most representative nail); by clinical evaluation of the nail fragility with a score; and by self-assessment (at days 14, 24, and 28 (D14, D28 and D84)) using target questionnaires.

The acceptability was checked every day, by the subjects themselves at home; controlled by the dermatologist or the technician, under their authority, and after questioning of the subjects, after products application.

The compatibility was controlled after visual examination of the experimental area, by the dermatologist or the technician, under their authority, and after questioning of the subjects, after product application.

According to the obtained results, the formulation of example 1 had very good acceptability and compatibility under normal conditions of use. Regarding instrumental measurements, the formulation of example 1 presented:
- A significant increase in the thickness of the superficial layer, after 28 and 84 days of product application.
- A significant increase in nail density, after 28 and 84 days of product application.
- A significant decrease in Ra roughness parameter, after 14, 28 and 84 days of product application.
- A significant decrease in Rz roughness parameter, after 28 and 84 days of product application.
- A significant decrease Nail grading system and therefore an improvement in nail appearance, after 14, 28 and 84 days of product application.

Antifungal Activity of Rhamnose-Rich Polysaccharide
Study 1

Human skin explants were obtained with informed consent from healthy, 40 to 55 year-old women undergoing plastic surgery (Authorisation granted by French government ethical committee according to French law L.1245 CSP). Up to 2 h from the surgery the skin was cut to a 0.8 $cm^2$ pieces and samples were placed with dermis facing down and epidermis facing up in culture plates containing DMEM medium with antibiotics (1% pen-strep). Cultures were incubated for at least 48 hours at 37° C. under 5% $CO_2$ for recovery prior to study initiation.

Step 1. Skin explants (Human Skin Explants) from healthy donors were altered by stripping (leading to removal of ~40% of stratum corneum thickness) to facilitate stabilization of infection by the fungus.

Step 2. The skin explants were allowed to stabilize (rested for 48 h) after stripping.

Step 3. For each treatment group test compositions (comparative example 3 (P1), and example 2 (P2)) were applied topically at 2 $mg/cm^2$ in a manner that was identical for all treatment groups and spread carefully using a microspatula. Skin explants in the Control group did not receive any topical treatment (control C).

Step 4. Skin explants previously coated with test articles and in Control group were inoculated by addition of a suspension of *Malassezia furfur* in the surface and incubated for 24 hours.

Step 5. After incubation period of 24 hours, the number of colony forming units (CFUs) was quantified using the direct plate method.

The antifungal activity was evaluated for piroctone olamine of comparative example 3 (P1), and the composition of example 2 (P2) with respect to control (C). As it can be seen in FIG. 1, the application of the compound of the invention (P2) effectively reduced the *M. furfur* growth.

Study 2

In this study an infection of the nail bed such as distal subungual onychomycosis which invades the nail bed and the underside of the nail plate was mimicked, by testing the compositions of the invention against *Candida albicans* (isolated from infected nail).

Human skin explants were obtained as in study 1 and were cut to a 0.8 $cm^2$ pieces. Samples were placed with dermis facing down and epidermis facing up in culture plates containing DMEM medium with antibiotics (1% pen-strep). Cultures were incubated for at least 48 hours at 37° C. under 5% $CO_2$ for recovery prior to study initiation. An inoculum of *Candida albicans* (106 CFUs) was prepared previously.

Figure 2:
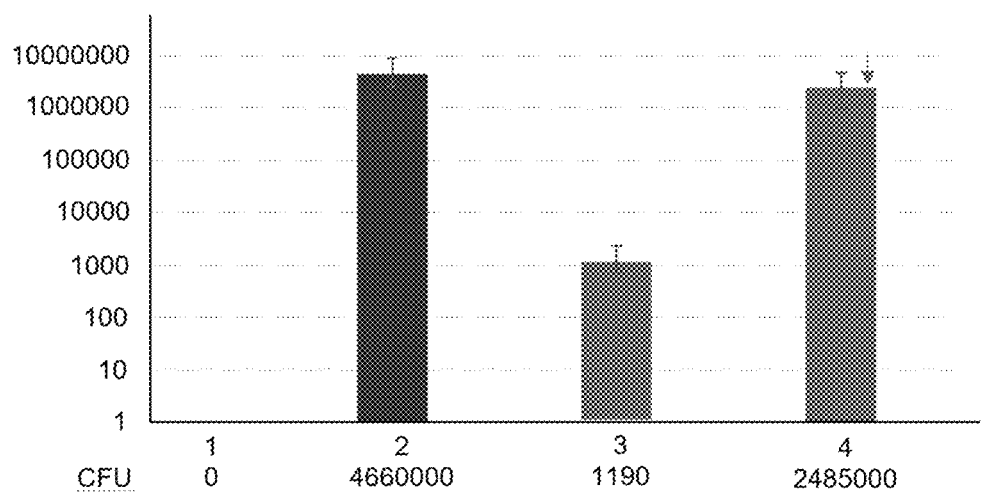
FIG. 2 shows an ex-vivo determination of the antifungal activity against *Candida albicans* in human skin explants of the composition of example 1 when applied at the same time of *Candida* inoculation (group 3) and of the same composition when applied 6 hours before the inoculum (group 4). Groups 1 and 2 are control groups: the non-treated non inoculated group, and to the inoculated non-treated group, respectively.

After 48 hours of conditioning of explants the explants were divided into four different groups:

1) Explants not inoculated and not treated (Control, group 1 FIG. 2)
2) Explants inoculated with *C. albicans* (inoculated Control, group 2 FIG. 2)
3) Explants inoculated with *C. albicans* and treated with the test composition at the same time (group 3 FIG. 2)
4) Explants treated first with the test composition and after 6 hours *C. albicans* inoculum was applied (group 4 FIG. 2).

For each treatment group test compositions (composition of example 1) were applied topically at 2 $mg/cm^2$ in a manner that was identical for all treatment groups and spread carefully using a microspatula.

5) After incubation period of 24 hours, the number of colony forming units (CFUs) was quantified using the direct plate method.

6) Gram staining was conducted

The activity of the product to resist *C. albicans* infection was evaluated by the comparison of CFUs for inoculated control vs. group 3 and 4. As it can be seen in FIG. 2, the application of the compound of the invention (groups 3 and 4) effectively reduced the *C. albicans* growth by 99% when applied at the same time as the inoculum (group 3), and by 46.7% when applied prior to the inoculum (group 4). The results suggest that the product provides clear protection of the concerned tissues against fungal infection.

Clinical Study
Case 1

A 58-year-old man with type 1 diabetes and *Candida* onychomycosis of 2 fingernails was treated topically in the affected nails with the composition of the invention (composition of example 1) twice a day for 6 months. After treatment a significant improvement in the fingernails could be observed.

Case 2

A 45-year-old woman with onychomycosis of the first right toenails due to *Trichophyton interdigitale* was treated with the composition of the invention (composition of example 1) twice a day for 3 months. After treatment it could be observed that the onychomycosis had been cured without the need for further therapy.

CITATION LIST

Prohic A., et al., "*The Prevalence* and Species *Composition of Malassezia yeasts in Patients with Clinically Suspected Onychomycosis*", Med. Arh. 2015 April; 69(2): 81-84.

Westerberg, D. P., et al. "*Onychomycosis: Current Trends in Diagnosis and Treatment*", Am Fam Physician. 2013 Dec. 1; 88(11):762-770.

The invention claimed is:
1. A combination comprising:
a) rhamnose or a rhamnose-rich polysaccharide, wherein the rhamnose-rich polysaccharide comprises rhamnose in an amount equal or higher than 30% w/w;
b) a film-forming agent;
c) an extract of *Pistacia lentiscus*; and
d) one or more further active agents selected from:
i) a hyaluronic acid derivative selected from the group consisting of hyaluronic acid, a pharmaceutically or cosmetically acceptable salt thereof, and a cationized hyaluronic acid, wherein the cationized hyaluronic acid is a hyaluronic acid wherein the hydrogen atom of at least one of the hydroxylic groups or the carboxylic group is replaced by a moiety of formula (III):

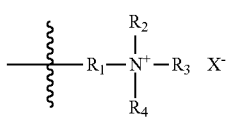

wherein each of $R_1$-$R_4$ independently represents a linear or branched ($C_1$-$C_6$)alkyl group optionally substituted with one or more hydroxyl groups, and X is a halogen ion; and ii) a silanol compound.

2. The combination according to claim 1, wherein the combination comprises the hyaluronic acid derivative as defined in claim 1; and the silanol compound as further active agents.

3. The combination according to claim 1, wherein a) is rhamnose-rich polysaccharide, and wherein the rhamnose-rich polysaccharide comprises a repeating unit of formula (I)

wherein each of $R_1$-$R_4$ independently represents a linear or branched ($C_1$-$C_6$)alkyl group optionally substituted with one or more hydroxyl groups, and X is a halogen ion.

6. The combination according to claim 1, wherein the silanol compound is a silanediol or a silanetriol.

7. The combination according to claim 1, wherein the film-forming agent is an acrylate polymer.

8. The combination according to claim 7, wherein the acrylate polymer is acrylates copolymer.

9. A pharmaceutical or cosmetic topical nail composition comprising the combination as defined in claim 1, together with one or more pharmaceutically or cosmetically acceptable excipients or carriers.

10. The pharmaceutical or cosmetic topical nail composition according to claim 9, wherein rhamnose or a rhamnose-rich polysaccharide is present in an amount from 0.03 to 0.07 wt % with respect to the weight of the total composition.

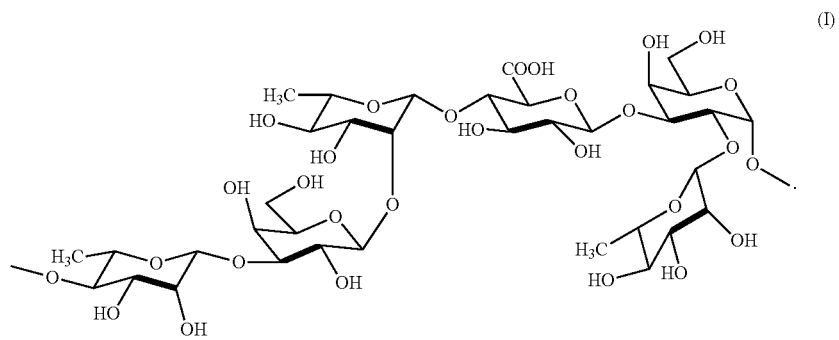

4. The combination according to claim 1, wherein the hyaluronic acid derivative is a cationized hyaluronic acid.

5. The combination according to claim 4, wherein the cationized hyaluronic acid has the formula (II):

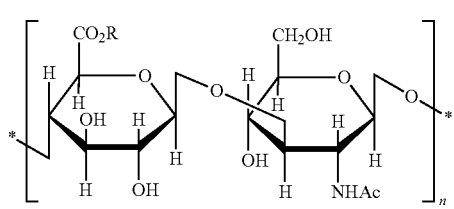

wherein R is a moiety of the formula (III):

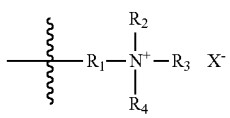

11. The pharmaceutical or cosmetic topical nail composition according to claim 9, wherein the film-forming agent in an amount from 0.1 to 0.5 wt % with respect to the weight of the total composition.

12. The pharmaceutical or cosmetic topical nail composition according to claim 9, wherein the composition comprises the hyaluronic acid derivative in an amount from 0.08 to 0.5 wt % with respect to the weight of the total composition.

13. The pharmaceutical or cosmetic topical nail composition according to claim 9, wherein the composition comprises the silanol compound in an amount from 0.15 to 0.5 wt % with respect to the weight of the total composition.

14. The pharmaceutical or cosmetic topical nail composition according to claim 9, wherein the composition comprises an extract of *Pistacia lentiscus* in an amount from 0.02 to 0.1 wt % with respect to the weight of the total composition.

15. The combination according to claim 2, wherein a) is rhamnose-rich polysaccharide, and wherein the rhamnose-rich polysaccharide comprises a repeating unit of formula (I)

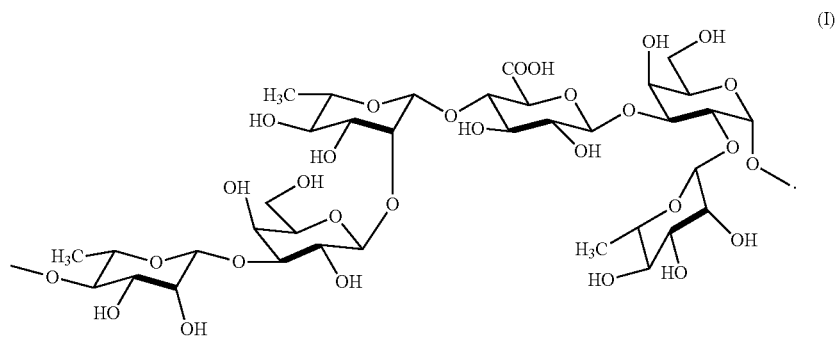

16. The combination according to claim 15, wherein the hyaluronic acid derivative is a cationized hyaluronic acid, and wherein the cationized hyaluronic acid has the formula (II):

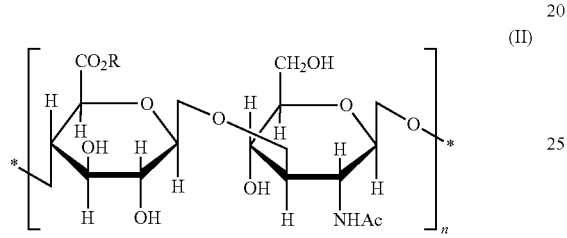

wherein R is a moiety of the formula (III):

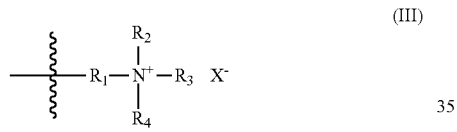

wherein each of $R_1$-$R_4$ independently represents a linear or branched ($C_1$-$C_6$)alkyl group optionally substituted with one or more hydroxyl groups, and X is a halogen ion.

17. The combination according to claim 16, wherein the silanol compound is a silanediol or a silanetriol.

18. The combination according to claim 17, wherein the film-forming agent is an acrylate polymer, and wherein the acrylate polymer is acrylates copolymer.

19. The pharmaceutical or cosmetic topical nail composition according to claim 9, wherein in the combination a) is rhamnose-rich polysaccharide, and wherein the rhamnose-rich polysaccharide comprises a repeating unit of formula (I)

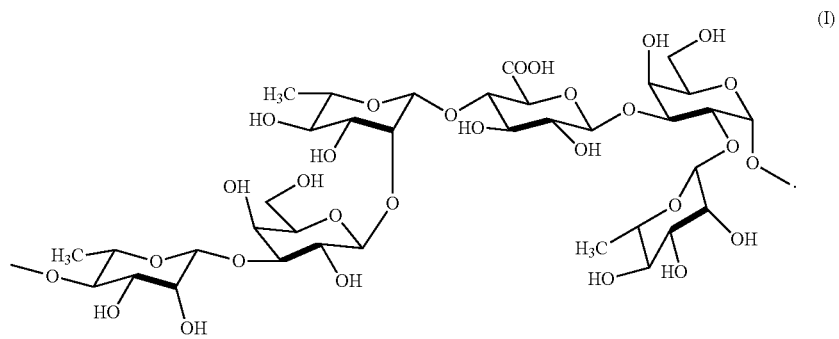

* * * * *